(12) United States Patent
Weinstock

(10) Patent No.: US 12,383,176 B2
(45) Date of Patent: Aug. 12, 2025

(54) SEALING CAP FOR SEALING A SAMPLE TUBE FOR RECEIVING A LIQUID

(71) Applicant: Sarstedt AG & Co. KG, Nümbrecht (DE)

(72) Inventor: Mark Weinstock, Helmenzen (DE)

(73) Assignee: Sarstedt AG & Co. KG, Nümbrecht (DE)

( * ) Notice: Subject to any disclaimer, the term of this patent is extended or adjusted under 35 U.S.C. 154(b) by 747 days.

(21) Appl. No.: 17/606,297

(22) PCT Filed: Jun. 16, 2020

(86) PCT No.: PCT/EP2020/066578
§ 371 (c)(1),
(2) Date: Oct. 25, 2021

(87) PCT Pub. No.: WO2020/260066
PCT Pub. Date: Dec. 30, 2020

(65) Prior Publication Data
US 2022/0202328 A1    Jun. 30, 2022

(30) Foreign Application Priority Data
Jun. 26, 2019    (DE) .................. 10 2019 117 240.3

(51) Int. Cl.
*A61B 5/15*    (2006.01)
*B01L 3/00*    (2006.01)

(52) U.S. Cl.
CPC .. *A61B 5/150351* (2013.01); *A61B 5/150221* (2013.01); *A61B 5/150755* (2013.01);
(Continued)

(58) Field of Classification Search
CPC ........ A61B 5/150221; A61B 5/150351; A61B 5/150755; B01L 3/5021; B01L 3/50825;
(Continued)

(56) References Cited

U.S. PATENT DOCUMENTS 3,976,579 A * 8/1976 Bennett .............. B01L 3/50215
422/918
4,150,089 A    4/1979 Linet
(Continued)

FOREIGN PATENT DOCUMENTS

AT    514833    7/2015
CN    1886308 A    12/2006
(Continued)

*Primary Examiner* — Charles A Marmor, II
*Assistant Examiner* — Abel Seifu Abegaz
(74) *Attorney, Agent, or Firm* — Smartpat PLC

(57) ABSTRACT

A sealing cap seals a sample tube for receiving a liquid, in particular blood. The sealing cap includes a cavity delimited by a membrane and a base having an opening that can be sealed by a non-return valve. In order to reduce the volume of liquid which, during centrifugation of the sample tube sealed by the sealing cap, flows out of the sealing cap through the then open opening into the sample tube, the cavity of the sealing cap has a separating wall that divides the cavity into a first and a second sub-area. Only the second sub-area is above the opening, also meaning that only the volume of liquid in the second sub-area can flow into the sample tube.

6 Claims, 5 Drawing Sheets

(52) U.S. Cl.
CPC ........... B01L 3/50825 (2013.01); B01L 3/567 (2013.01); *B01L 2200/141* (2013.01); *B01L 2300/044* (2013.01); *B01L 2300/047* (2013.01); *B01L 2300/049* (2013.01)

(58) Field of Classification Search
CPC ............... B01L 3/567; B01L 2300/042; B01L 2300/044; B01L 2300/047; B01L 2300/049
See application file for complete search history.

(56) References Cited

U.S. PATENT DOCUMENTS

| | | | |
|---|---|---|---|
| 4,152,269 A | * | 5/1979 | Babson ................. A61J 1/1406 215/DIG. 8 |
| 2005/0154368 A1 | | 7/2005 | Lim et al. |
| 2007/0134134 A1 | | 6/2007 | Watts et al. |
| 2008/0017577 A1 | | 1/2008 | Yi et al. |
| 2008/0121050 A1 | | 5/2008 | Sakal et al. |
| 2011/0005622 A1 | | 1/2011 | Boeckeler |
| 2014/0309556 A1 | | 10/2014 | Fletcher et al. |
| 2016/0278680 A1 | | 9/2016 | Bauer et al. |
| 2016/0332158 A1 | | 11/2016 | Leach et al. |
| 2016/0334307 A1 | | 11/2016 | Ragusa et al. |
| 2017/0059552 A1 | | 3/2017 | Campton et al. |
| 2018/0250669 A1 | | 9/2018 | Adamski et al. |
| 2019/0046976 A1 | | 2/2019 | Ronsick et al. |
| 2019/0200908 A1 | | 7/2019 | Connolly et al. |
| 2019/0209065 A1 | | 7/2019 | Connolly et al. |
| 2020/0069521 A1 | | 3/2020 | Garau et al. |

FOREIGN PATENT DOCUMENTS

| | | |
|---|---|---|
| CN | 101321586 A | 12/2008 |
| CN | 104107056 A | 10/2014 |
| JP | 2001159630 A | 6/2001 |
| JP | 2005287955 A | 10/2005 |
| JP | 2008279195 A | 11/2008 |
| RU | 2485033 | 9/2013 |
| WO | 2005062751 A2 | 7/2005 |
| WO | 2008067215 A2 | 6/2008 |
| WO | 2015106191 A1 | 7/2015 |
| WO | 2017162574 A1 | 9/2017 |
| WO | 2017181020 A1 | 10/2017 |
| WO | 2018015568 A1 | 1/2018 |
| WO | 2018109246 A1 | 6/2018 |

* cited by examiner

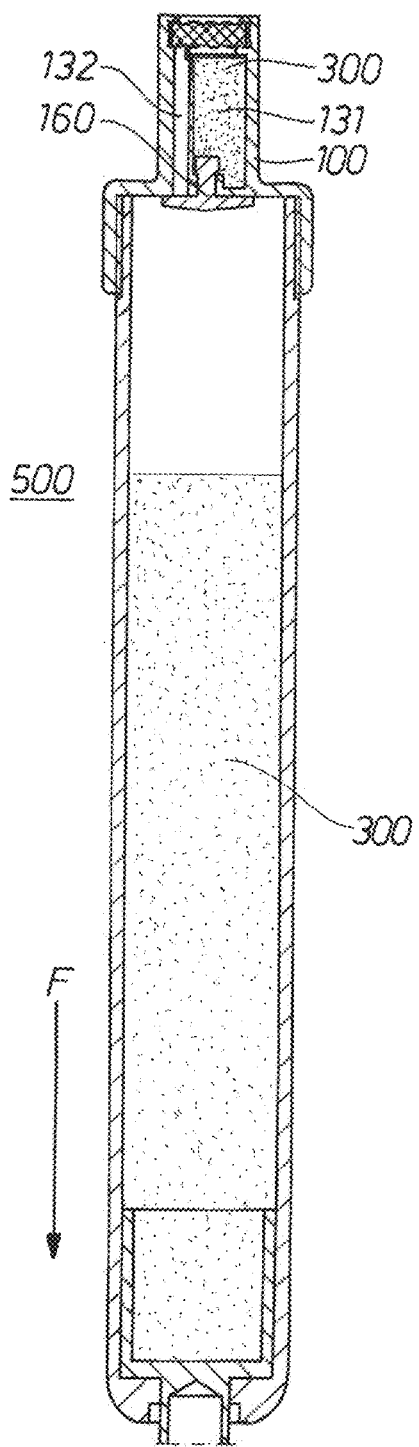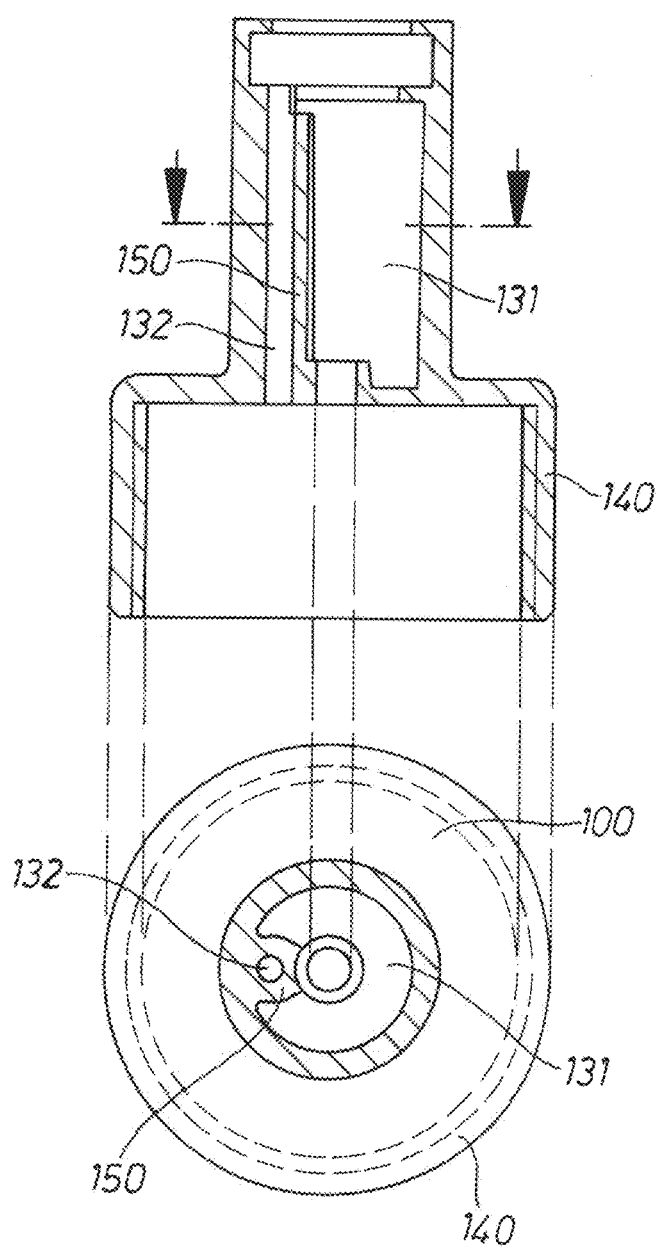

SEALING CAP FOR SEALING A SAMPLE TUBE FOR RECEIVING A LIQUID

TECHNICAL FIELD

The invention relates to a sealing cap for sealing a sample tube for receiving a liquid, in particular a human or animal liquid, further in particular blood. The disclosure also relates to a blood collection tube comprising, inter alia, the sealing cap in accordance with the disclosure and a method for handling the blood collection tube.

BACKGROUND

The main requirement for a blood collection tube, consisting of a sample tube and a sealing cap, for taking samples of fluids from a body, is that it seals tightly and prevents the contamination of the samples.

From the international patent application WO2017/162 574 A1 along with the Japanese patent application JP2005 287 955, sealing caps for sample tubes are known in principle. The sealing caps comprise a non-return valve on their side facing the sample tube. The opposite side is sealed by a membrane that can be punctured with a cannula. A cavity is formed between them. The cannula can be used to withdraw a fluid, for example from a human or animal body. The liquid from the body flows through the cannula into the cavity in the sealing cap and then through the non-return valve into the sample tube. When the cannula is pulled out of the sealing cap, the membrane seals automatically. An appropriate design of the non-return valve ensures that the sample tube is securely sealed against leakage of the liquid. Various embodiments are disclosed for non-return valves, each of which opens under the action of a centrifugal force in the axial direction of the sample tubes.

To prepare fluid from the body, in particular blood for later analysis, it is common and necessary to separate it into its light and heavy components. This is typically done by centrifuging the fluid in the blood collection tube.

Before a sample is taken, that is before the blood collection tube is filled with the liquid, an anticoagulant or a coagulation accelerator, both of which are also referred to below as preparation, is usually introduced into the sample tube by the manufacturer. In the blood collection tube, the preparation mixes with the incoming liquid. The preparation ensures that the blood components are available for later analysis in a desired clotted or non-clotted state.

To achieve the desired coagulation state, it is important to maintain a predetermined quantitative ratio between liquid and preparation.

In the embodiments proposed in the above prior art, there is still a relatively large residual amount of liquid in the cavity of the sealing cap after sampling.

Due to the typical preparation of a sample in a centrifuge, a tensile force is exerted in the axial direction on the installed non-return valve, causing it to open. The relatively large amount of liquid contained in the cavity of the sealing cap enters the sample tube, where it contaminates the sensitive sample material with the blood that has coagulated and become hemolyzed by then. This can negatively influence the results of the subsequent analysis.

Transport processes, such as those that can occur in a tube delivery system, also pose the risk of contamination of the liquid by liquid residues stored upstream of the valve that still originate from the blood collection.

SUMMARY

The invention improves a known sealing cap for sealing a sample tube, a known blood collection tube and a known method for handling the blood collection tube in such a way that the volume of the liquid that flows out of the sealing cap into the sample tube during centrifugation of the blood collection tube is reduced and delimited in such a manner that it does not lead to any disruption during subsequent analysis of the liquid, in particular of blood, or that the result of the analysis is not falsified.

The improved sealing cap is characterized in that the cavity comprises a separating wall for dividing the cavity into first and second sub-areas; in that the first sub-area is formed above a region of the base without the opening; in that the second sub-area is formed above the opening in the base; and in that the first and second sub-areas are formed above the base in a manner in fluid communication with each other.

The cavity in the sealing cap is divided into at least two sub-areas. For this reason, the volume of each of the sub-areas is smaller than volume of the original whole cavity. Only the amount of liquid from the second sub-area can flow into the sample tube during a centrifugation of the blood collection tube, because only the second sub-area is formed above the opening. In this manner, it is ensured that only a part of the volume of liquid found in the entire cavity of the sealing cap can flow into the sample tube. In this respect, the volume of liquid draining into the sample tube is advantageously reduced compared to the total volume of liquid enclosed in the cavity of the sealing cap.

In this application, the term "fluid" is used to refer to fluids that can be withdrawn from a human or animal body, in particular blood.

"Preparation" refers to a defined amount of an active ingredient (anticoagulant or coagulation accelerator) to adjust a desired coagulation property of a liquid, for example in a sample tube.

A "non-return valve" can also be formed as a one-piece sealing element within the scope of the present disclosure.

The volume of the second sub-area and, accordingly, the residual amount of body fluid or blood, as the case may be, that only flows into the sample tube are dimensioned so small that the adverse effect on the ratio of body fluid to preparation in the sample tube caused by them is negligible; in particular, the residual amount is so small that subsequent analysis of the (blood) sample taken is possible without any appreciable falsification.

In accordance with a first exemplary embodiment, the volume of the first cavity is larger than the volume of the second cavity. Accordingly, the second sub-area is smaller than the first sub-area. The smaller and larger sub-areas together make up at least a partial volume of the entire cavity. The term "larger sub-area" does not rule out that the larger sub-area is in turn subdivided again into a plurality of smaller chambers, the individual volumes of which can also be even smaller than the volume of the smaller sub-area. However, none of the chambers then have an opening in their respective bases.

In accordance with further embodiments, the separating wall is configured such that the separating wall comprises, at its end facing the membrane, an overflow edge and/or a perforation, for enabling fluid communication between the second, preferably larger, and the first, preferably smaller, sub-area. Thereby, the separating wall can extend into the cavity from the base of the cavity.

A further exemplary blood collection tube is characterized in that it comprises, on the one hand, the sample tube having a sealable end for receiving the liquid and, on the other hand, the sealing cap for sealing the sample tube at its sealable end.

A method for handling the blood collection tube has advantages which correspond to the advantages mentioned above with reference to the claimed sealing cap.

BRIEF DESCRIPTION OF THE DRAWINGS

FIG. 5: Illustration of the sealing cap with connected sample tube;
and
FIG. 6 Illustration of a cross-section through the sealing cap.

DETAILED DESCRIPTION

The invention is described in detail below with reference to the specified figures in the form of exemplary embodiments. In all figures, the same technical elements are designated with the same reference signs.

Figure 1:
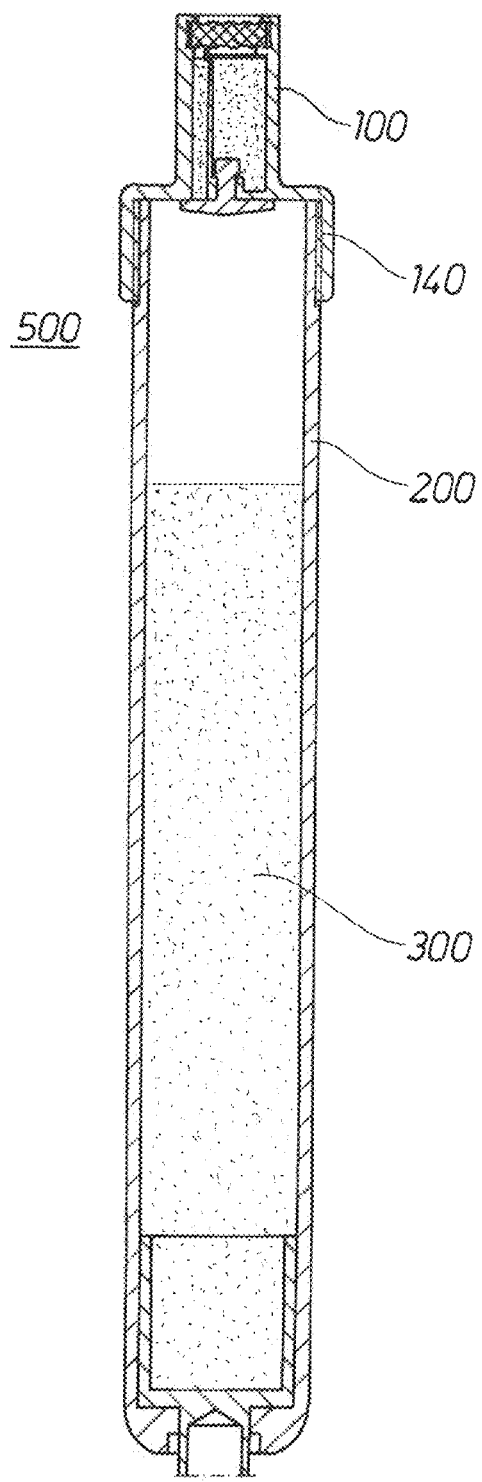
FIG. 1: Illustration of the blood collection tube.

FIG. 1 depicts a blood collection tube 500 consisting of a sealing cap 100 and a sample tube 200 for receiving a fluid 300 from a human or animal body.

Preferably, the sealing cap 100 comprises a connecting part 140 for connecting the sealing cap 100 to the sample tube 200 or for sealing the sample tube 200, as the case may be. The connecting part 140 can be configured as a screw, bayonet or plug-in connection. The connection must be liquid-tight and/or air-tight according to the requirements. It may be necessary to use additional sealants for this purpose. The connecting part may also be completely dispensable, for example if the sealing cap is simply plugged onto the sample tube.

Figure 2:
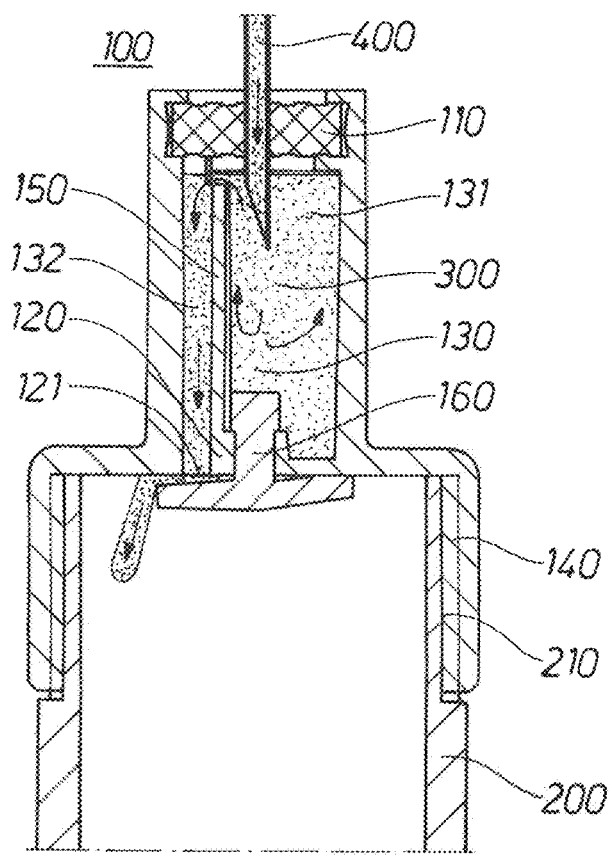
FIG. 2: Illustration of the flow-through sealing cap.

FIG. 2 shows an illustration of the sealing cap 100 through which a liquid 300 flows and which seals the sample tube 200. A cavity 130 is formed in the sealing cap 100, which is delimited by a membrane 110 and a base 120. An opening 121 is formed in the base, which can be opened or sealed by a non-return valve 160. The non-return valve 160 is configured to allow fluid 300 to flow from the cavity 130 in the sealing cap 100 into the sample tube 200, but to block the opposite direction.

The membrane 110 can be pierced by a cannula 400. The cannula 400 establishes a fluid-conducting connection between the sealing cap 100 and the body from which the fluid is withdrawn, and directs the fluid 300 into the cavity 130 of the sealing cap 100. The cavity 130 is divided by a separating wall 150 into a first, preferably larger, sub-area 131 and a second, preferably smaller, sub-area 132. The larger sub-area 131 does not have an opening 121 in its base 120. The smaller sub-area 132 is formed above the opening 121 in the base 120. For example, the volume of the smaller sub-area is in a range between 0-70 μl (microliter).

Figure 3:
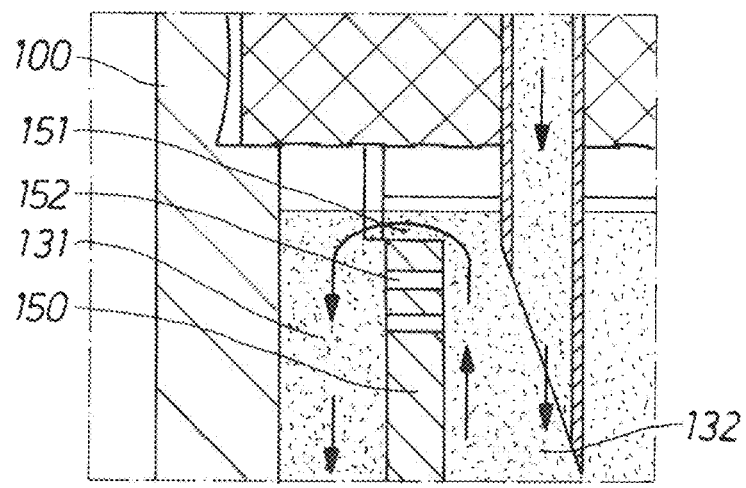
FIG. 3: Illustration of a detail from FIG. 2 showing an overflow edge or perforation, as the case may be.

The design of the separating wall 150 is such that a flow-through area is created between the two sub-areas 131, 132. The flow-through area can result from a gap between an overflow edge 151 of the separating wall 150 and the membrane 110 above it and/or a perforation 152 in the separating wall 150 (FIG. 3). The flow-through area must be large enough to ensure sufficient liquid flow during sampling. Both sub-areas 131/132 are thus connected to each other in a fluid-conducting communicating manner. The separating wall 150 preferably extends from the base 120 of the sealing cap in the direction of the membrane 110.

The vector arrows in FIG. 2 indicate a direction of flow of the fluid 300 through the two sub-areas 131/132 and the opened sealing element 161 into the sample tube 200.

The handling method in accordance with the disclosure is described below with reference to FIGS. 2 to 5. The sealing cap 100 is used to seal a sealable end 210 of the sample tube 200. Prior to sealing, a preparation can be added to the sample tube 200. The optional insertion of the preparation and/or the necessary sealing of the blood collection tube can be performed by the manufacturer. The blood collection tube 500 thus assembled can be filled with the fluid 300.

For this purpose, the body is punctured, for example with a cannula 400. One side of the cannula 400 pierces the body, and the other side pierces the membrane 110 in the sealing cap 100, see FIG. 4a.

The fluid 300 flows out of the body through the cannula 400 into the cavity 130 of the sealing cap 100, due to an existing negative pressure in the sample tube. Depending on the type of construction of the blood collection tube, the vacuum in it is already introduced there by the manufacturer. Other blood collection techniques, such as the vacuum principle or the aspiration principle, are conceivable. Interaction by the user is then required to build up pressure in the sample tube.

If a plunger or piston, as the case may be, of the sample tube is manually pulled into a rear locking position before puncturing a vein in the body, the vacuum in the blood collection tube is thereby built up only if required shortly prior to blood collection and the collection of the blood then takes place analogously to the manufacturer's pre-evacuated tube with vacuum technology (vacuum principle). We speak of aspiration technique when coupling with the vein occurs initially and blood sampling occurs in parallel with the piston stroke.

Figure 4A:
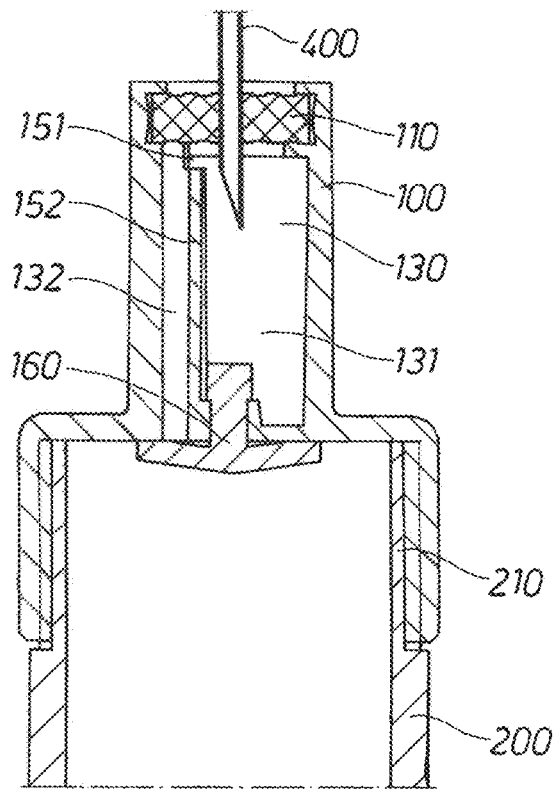
FIGS. 4a-d: Illustration of the filling process of the sealing cap over time.
Figure 4B:
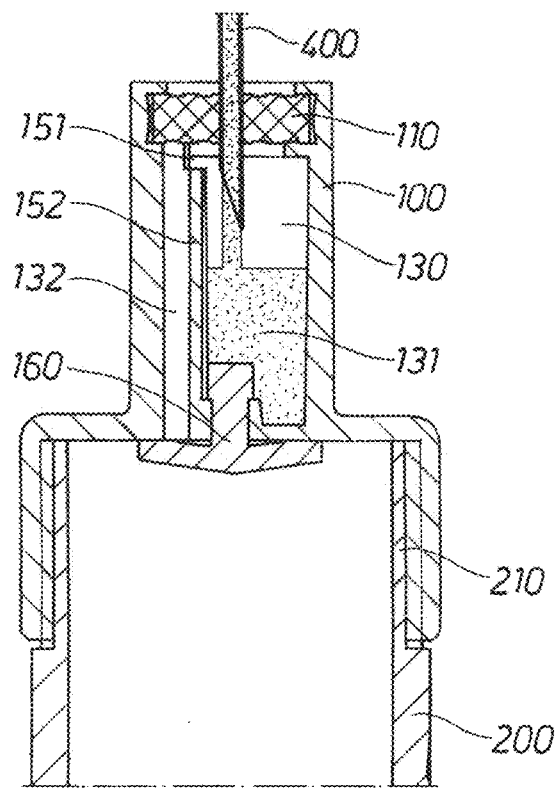
Figure 4C:
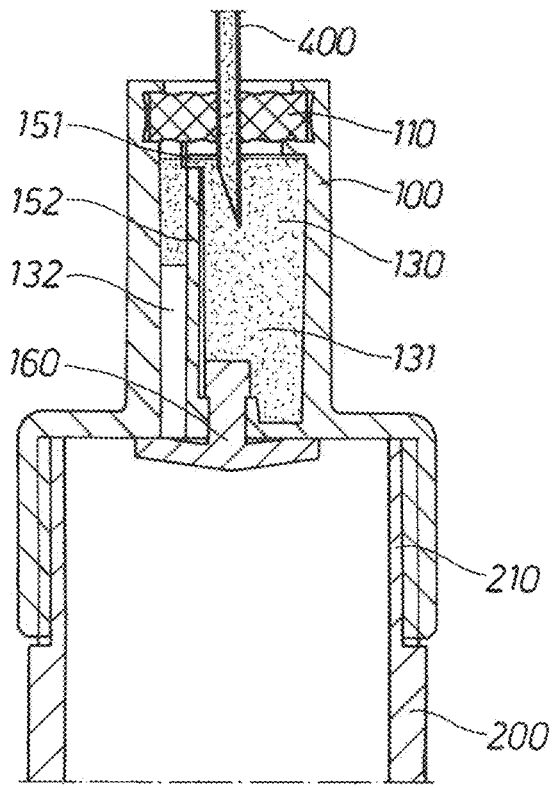
Figure 4D:
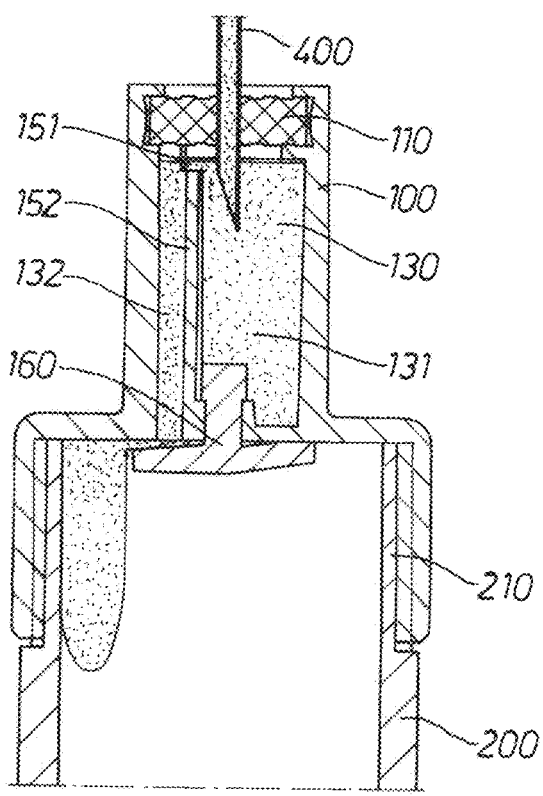

In the cavity 130 of the sealing cap 100, the large sub-area 131 is preferably filled initially, see FIG. 4b. Subsequently, the liquid 300 flows over the overflow edge 151 and/or through the perforation 152 into the small sub-area 132, see FIG. 4c. Optionally, only the smaller sub-area can be filled.

Due to an existing pressure difference between the negative pressure in the sample tube 200 and the pressure in the sealing cap 100, the non-return valve 160 opens during a blood sample collection. The liquid 300 then drains from the sealing cap 100, and in particular from its smaller sub-area, into the sample tube 200, see FIG. 4d.

Once the sample tube 200 is sufficiently filled with the fluid 300, the sampling is interrupted by cutting off the fluid line between the body and the blood collection tube. This results in a pressure equalization in the blood collection tube; in particular, it relieves the negative pressure in the sample tube. Once the pressure difference between the blood collection tube 500 and the volume 130 in the sealing cap 100 is equalized, this causes the non-return valve 160 to close again. The sample tube 200 is then sealed in a fluid-conducting manner with respect to the sealing cap.

Upon a processing of the liquid 300 in the blood collection tube 500 in a centrifuge, which follows the sampling, a force F directed towards the base of the sample tube acts on the blood collection tube 500; see the arrow in FIG. 5. This causes the heavy components to separate from the light components in the liquid 300. This force F, if sufficient, will also reopen the non-return valve 160 and the liquid 300 will flow unintentionally from the cavity of the sealing cap into the sample tube 200.

However, as shown in FIG. 5, only the volume of liquid from the second, preferably smaller, sub-area 132 flows into the sample tube 200. In contrast, the liquid 300 remains in the first, preferably larger, sub-area 131 in the sealing cap 100.

If the dimensions of the second, preferably smaller, sub-area 132 in the sealing cap 100 are sufficiently small relative to the total amount of liquid in the sample tube, the quality of the liquid required for subsequent analysis can be ensured, even if the liquid 300 flows from the smaller sub-area 132 into the sample tube 200.

FIG. 6 shows a cross-section through the sealing cap 100 in accordance with the invention. In particular, an exemplary arrangement and configuration for the separating wall 150 and for the larger sub-area 131 and the smaller sub-area 132 can be seen.

REFERENCE SIGNS

100 Sealing cap
110 Membrane
120 Base
121 Opening
130 Cavity
131 First, preferably larger sub-area
132 Second, preferably smaller sub-area
140 Connecting part
150 Separating wall
151 Overflow edge
152 Perforation
160 Non-return valve
170 Sealing region
200 Sample tube
210 Sealable end
300 Liquid
400 Cannula
500 Blood collection tube

The invention claimed is:

1. A sealing cap (100) for sealing a sample tube (200) containing blood (300), comprising:
a membrane (110) that can be pierced by a cannula (400);
a base (120) arranged below the membrane, the base (120) having an opening (121);
a cavity (130) formed between the membrane (110) and the base (120) for receiving the blood (300); and
a non-return valve (160) arranged at the base (120) and configured for unblocking the opening (121) in the base (120) to allow the blood (300) to flow out of the cavity (130) into the sample tube (200) and for sealing the opening (121) to not allow the blood (300) to flow out of the sample tube (200) into the cavity (130),
wherein the cavity (130) has a separating wall (150) for dividing the cavity into a first sub-area (131) and a second sub-area (132),
wherein the separating wall (150) extends into the cavity (130) from the base (120) of the cavity (130),
wherein the first sub-area (131) is formed above a region of the base (120) without the opening (121),
wherein the second sub-area (132) is formed above the opening (121) in the base (120), and
wherein the first sub-area (131) and the second sub-area (132) are in fluid communication with each other, and
wherein the separating wall (150) comprises, at an end facing the membrane (110), an overflow edge (151) and/or a perforation (152), for enabling the fluid communication between the first sub-area (131) and the second sub-area (132).

2. The sealing cap (100) according to claim 1, wherein the first sub-area (131) is larger than the second sub-area (132).

3. The sealing cap (100) according to claim 1, wherein the non-return valve (160) is directly coupled to the opening (121) in the base (120).

4. A blood collection tube (500) comprising:
a sample tube (200) for receiving blood (300) having a sealable end (210); and
the sealing cap (100) according to claim 1 for sealing the sample tube at its sealable end (210).

5. A method for handling the blood collection tube (500) according to claim 4, comprising the steps of:
sealing the sample tube (200) at its sealable end (210) with the sealing cap (100);
piercing the membrane (110) in the sealing cap (100) with one end of a cannula (400);
withdrawing blood (300) from a body with the other end of the cannula (400), wherein the blood (300) flows through the cannula (400) and the membrane (110) into the cavity (130) of the sealing cap (100) and subsequently flows through the opening (121) in the base (120) of the sealing cap (100), which is opened in a flow direction by the non-return valve (160), into the sample tube and fills it;
removing the cannula (400) from the membrane (110), whereupon the membrane (110) automatically seals again; and
centrifuging the blood collection tube (500) to separate the blood (300) into heavier and lighter components, wherein the non-return valve (160) releases the opening (121) in the base (120) of the sealing cap (100) due to a centrifugal force, such that the blood (300) flows out of the cavity (130) into the sample tube (200);
wherein, upon the withdrawal of the blood (300), both the first sub-area (131) and the second sub-area (132) of the cavity (130), which are connected to one another in a fluid-conducting communicating manner, are filled with blood (300);
wherein during centrifugation, only blood (300) from the second sub-area (132), in the base (120) of which the opening (121) is formed, flows into the sample tube (200); and
wherein, upon withdrawing the blood from the body, the blood first flows into and fills the first sub-area (131) of the sealing cap (100), and then flows via the overflow edge (151) and/or through the perforation (152) into the second sub-area (132).

6. The method according to claim 5, wherein the sample tube (200) has been provided with a preparation for blood prior to sealing with the sealing cap (100).

* * * * *